United States Patent [19]

Leupold et al.

[11] 4,009,209
[45] Feb. 22, 1977

[54] DIMERIZATION OF CYCLOHEXYLIDENE-ACETONITRILE AND HYDROGENATION OF THE RESULTING SUBSTITUTED GLUTARIC ACID DINITRILE

[75] Inventors: Ernst Ingo Leupold, Hofheim, Taunus; Hans-Jürgen Arpe, Fischbach, Taunus, both of Germany

[73] Assignee: Hoechst Aktiengesellschaft, Frankfurt am Main, Germany

[22] Filed: Feb. 9, 1976

[21] Appl. No.: 656,706

Related U.S. Application Data

[60] Division of Ser. No. 567,053, April 11, 1975, which is a continuation-in-part of Ser. No. 460,152, April 11, 1974, abandoned.

[30] Foreign Application Priority Data

Apr. 13, 1973 Germany .......................... 2318676

[52] U.S. Cl. ..................... 260/563 P; 260/293.66; 260/464

[51] Int. Cl.² ......................................... C07C 87/34
[58] Field of Search ................................ 260/563 P

[56] References Cited

UNITED STATES PATENTS

| | | | |
|---|---|---|---|
| 3,152,184 | 10/1964 | Levering | 260/563 P X |
| 3,515,740 | 6/1970 | Frampton | 260/563 P X |
| 3,697,594 | 10/1972 | Knowles | 260/563 P X |
| 3,905,940 | 9/1975 | Zondler | 260/563 P X |

Primary Examiner—Paul F. Shaver
Attorney, Agent, or Firm—Curtis, Morris & Safford

[57] ABSTRACT

A process is provided for the dimerization of cyclohexylidene-acetonitrile to form 2-(1-cyclohexenyl)-3,3-pentamethylene-glutaric acid dinitrile and the hydrogenation thereof to form 1,5-diamino-2-(1-cyclohexenyl)-3,3-pentamethylene-pentane.

9 Claims, No Drawings

DIMERIZATION OF CYCLOHEXYLIDENE-ACETONITRILE AND HYDROGENATION OF THE RESULTING SUBSTITUTED GLUTARIC ACID DINITRILE

This application is a divisional of application Ser. No. 567,053 filed Apr. 11, 1975, which is a continuation-in-part of application Ser. No. 460,152 filed Apr. 11, 1975, now abandoned.

The present invention relates to a process for the dimerization of cyclohexylidene-acetonitrile (I) to form 2-(1-cyclohexenyl)-3,3-pentamethylene-glutaric acid dinitrile (II) and the hydrogenation thereof to form 3-aza-1-(1-cyclohexenyl)-spiro[5,5]undecane (V) via two isolable intermediate compounds: 2-cyclohexylidene-3,3-pentamethylene-5-aminovaleronitrile (III) and 1,5-diamino-2-(1-cyclohexenyl)-3,3-pentamethylene-pentane (IV) according to the following reaction scheme:

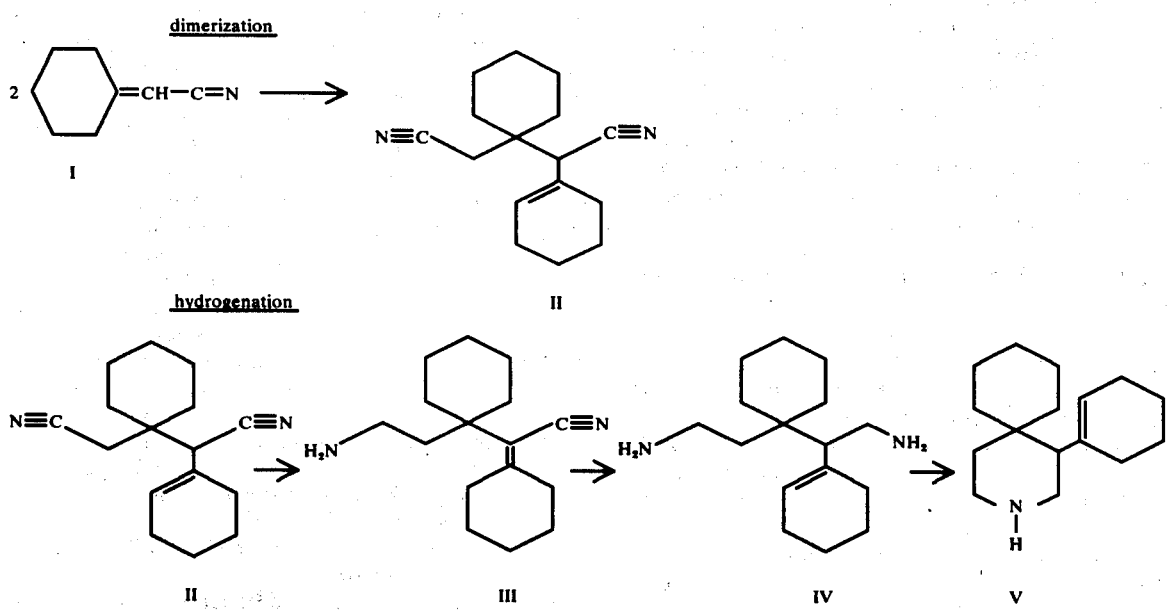

The following abbreviations are hereinafter used: "dinitrile" for the dimerization product (II), "aminonitrile" (III), "diamine" (IV) and "spiroamine" (V) for the hydrogenation products in the sequence of formulae of the above scheme.

It is already known that the dinitrile is obtained as by-product with poor yields from cyclohexanone and acetonitrile in the manufacture of cyclohexylidene-acetonitrile; but the literature does not indicate a special process for its preparation.

The present invention now provides a process for the preparation of the spiroamine 3-aza-1-(1-cyclohexenyl)-spiro[5,5]undecane of the formula

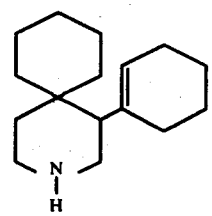

which process comprises dimerizing cyclohexylidene-acetonitrile in the liquid phase, in the presence of basic catalysts, at temperatures of from 0° to 200° C, to form the dinitrile 2-(1-cyclohexenyl)-3,3-pentamethylene-glutaric acid dinitrile of the formula

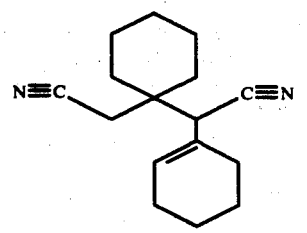

and hydrogenating this dinitrile in the presence of a hydrogenation catalyst containing preferably cobalt, at temperatures of from 50° to 250° C, in which process step the aminonitrile 2-cyclohexylidene-3,3-pentamethylene-5-aminovaleronitrile of the formula

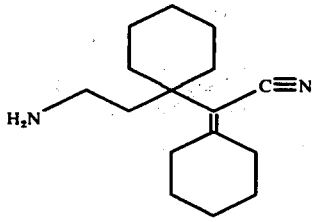

and the diamine 1,5-diamino-2-(1-cyclohexenyl)-3,3-pentamethylene-pentane of the formula

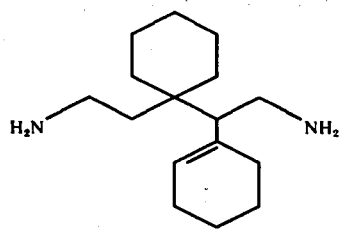

are obtained as isolable intermediate products.

The three hydrogenation products aminonitrile, diamine and spiroamine are novel compounds which hitherto have not yet been described.

The dinitrile is formed from cyclohexylidene-acetonitrile in the presence of a basic catalyst, generally in the absence of a solvent. However, the dimerization may also be carried out in usual inert solvents, for example benzene or hexane, and gives satisfying results.

In principle, all basic catalysts are suitable for the dimerization according to the process of the invention. Preferably, alkali metals and alkaline earth metals their alcoholates, amides or hydrides are used, but also mixtures of these compounds catalyze the dimerization in accordance with the present invention.

The concentration of the catalyst is advantageously from 0.1 to 10 mol %, relative to the cyclohexylidene-acetonitrile, but satisfying selectivities are also obtained when said limits are exceeded.

The dimerization of cyclohexylidene-acetonitrile according to the process of the invention may be carried out in any apparatus suitable for the reaction in the liquid phase.

The dimerization in accordance with the present invention may be carried out at temperatures of from 0° to 200° C, preferably from 20° to 120° C.

The reaction mixture is worked up according to usual methods: for example, after distilling off the non-reacted cyclohexylidene-acetonitrile, the dinitrile is generally obtained in the form of crystals, which may be further purified by distillation or recrystallization from methanol.

It is also possible and advantageous, especially at high conversion rates of cyclohexylidene-acetonitrile, to hydrogenate the reaction mixture directly without preliminary work-up of the aminonitrile and the diamine to form the spiroamine. In this case, the non-converted cyclohexylidene-acetonitrile is hydrogenated under the hydrogenation conditions to form β-cyclohexyl-ethylamine, which may be easily separated.

For the hydrogenation of the dinitrile according to the process of the invention, in principle all hydrogenation catalysts are suitable, for example platinum, rhodium, ruthenium, palladium, nickel or cobalt containing catalysts, the latter being preferred.

The amount of hydrogenation catalyst may widely vary; advantageously, from 0.1 to 20 g per mol of dinitrile are used. After the hydrogenation is complete, the catalyst may be isolated by simple filtration and reused.

For the hydrogenation of the dinitrile according to the present invention, an elevated hydrogen pressure of preferably from 50 to 500 bars is advantageous. However, satisfying results may also be obtained when these limits are exceeded.

The hydrogenation temperature is advantageously from 50° to 250° C. For the preparation of the aminonitrile, the temperatures are preferably from 50° to 100° C, for the preparation of the diamine preferably from 90° to 150° C, and for the preparation of the spiroamine preferably from 120° to 220° C.

Since a nitrile group linked to a primary carbon atom is more easily hydrogenated than a nitrile group linked to a secondary carbon atom, the aminonitrile is obtained in the first place from the dinitrile at relatively low hydrogenation temperatures, while at slightly elevated temperatures also the secondary nitrile group of the dinitrile is attained by the hydrogenation, and thus the diamine is obtained. At still higher temperatures, the diamine is cyclized to form the spiroamine with simultaneous hydrogenolytic separation of $NH_3$.

The hydrogenation in accordance with the present invention may be carried out in all solvents usually employed in hydrogenations, such as methanol, ethanol, hexane, acetic acid, tetrahydrofuran, acetic acid ethyl ester, but preferably in dioxan or mixtures of dioxan and liquid ammonia. When the hydrogenation is carried out in acetic anhydride, the N-acylated hydrogenation products may be obtained. The amount of solvent may widely vary. Advantageously, 0.1 to 10 molar solutions of the dinitrile are hydrogenated. Good results, however, are also obtained without the use of a solvent. Liquid ammonia is advantageously employed in the case where the preparation of the aminonitrile or the diamine is intended because, by this operation mode, the hydrogenolytic separation of $NH_3$, which causes formation of the spiroamine, is prevented. Therefore, the spiroamine is advantageously formed in the absence of ammonia.

The hydrogenation in accordance with the present invention may be carried out in any suitable apparatus, V4A autoclaves being preferred.

The hydrogenation products of the dinitrile are worked up according to known methods; for example, the main product may be separated by vacuum distillation, or recrystallization from dioxan or mixtures of n-pentane and methanol.

The three amines obtained by hydrogenation of the dinitrile are industrially interesting intermediate products, since the double bond and the amino groups allow a multitude of reactions. The diamine may be used directly without further chemical conversions as one of the comonomers (the other being a dicarboxylic acid) for the manufacture of polyamides, for example transparent polyamides. The polyamides are manufactured by reacting equal amounts of a diamine and a dicarboxylic acid. In a first step the components are combined in a water and alcohol solution to form a salt. In a second step an aqueous solution of the salt is subjected to heat and pressure. This causes the dissociation and subsequently formation of amide groups. The pressure is reduced and condensation is promoted to form a high-molecular-weight polymer.

The following examples illustrate the invention.

EXAMPLE 1

50 g of cyclohexylidene-acetonitrile and 2.5 g of potassium tert.-butylate are heated to 50°–80° C for 12 hours. The reaction product is then subjected to a vacuum distillation. The first fraction contains 12 g of non-reacted cyclohexylidene-acetonitrile (boiling point 90°C /10 mm), which corresponds to a conversion rate of 76%, and 35 g of 2-(1-cyclohexenyl)-3,3-pentamethylene-glutaric acid dinitrile (boiling point 160° C/1mm), corresponding to a selectivity of 92 %.

EXAMPLE 2

70 g of cyclohexylidene-acetonitrile and 1.3 g of NaH are heated to 100° C for 20 hours in a V4A autoclave under a nitrogen atmosphere. 200 ml of dioxan and 3 g of a catalyst containing 45 % of cobalt and 55 % of SiO$_2$ are added, and the whole is hydrogenated for 15 hours at 200° C under a hydrogen pressure of 290 bars. After evaporation of the dioxan, the residue is distilled. The main fraction, boiling point 110° C/0.05 mm, contains 55 g of pure 3-aza-1-(1-cyclohexenyl)-spiro-[5,5]-undecane, melting point 50° C, which corresponds to a yield of 76 %.

EXAMPLE 3

A mixture of 60 g of 2-(1-cyclohexenyl)-3,3-pentamethyleneglutaric acid dinitrile, 100 ml of dioxan, 55 g of liquid NH$_3$ and 3 g of Raney cobalt is intensely shaken for 24 hours at 80° C and a hydrogen pressure of 200 bars in a V4A autoclave. After the reaction mixture has become cold, the ammonia and the main part of the dioxan are evaporated. From the evaporation residue, 52 g of pure 2-cyclohexylidene-3,3-pentamethylene-5-aminovaleronitrile, melting point 148° C, crystallize, which corresponds to a yield of 85 %.

EXAMPLE 4

A mixture of 83 g of 2-(1-cyclohexenyl)-3,3-pentamethyleneglutaric acid dinitrile, 100 ml of dioxan, 105 g of liquid NH$_3$ and 1 g of Raney cobalt is hydrogenated, with intense shaking, for 45 hours at 120° C and a hydrogen pressure of 280 bars in a V4A autoclave. After evaporation of the dioxan/NH$_3$ mixture, the residue is distilled. The main fraction, boiling point 155° C/0.1 mm, is compsed of 70 g of 1,5-diamino-2-(1-cyclohexenyl)-3,3-pentamethylene-pentane, melting point 55° C, which corresponds to a yield of 81 %.

EXAMPLE 5

A mixture of 50 g of 2-(1-cyclohexenyl)-3,3-pentamethylene-glutaric acid dinitrile, 150 ml of dioxan and 4 g of a catalyst containing 45 % of cobalt and 55 % of SiO$_2$ is intensely shaken for 10 hours at 200° C and a hydrogen pressure of 320 bars in a V4A autoclave. After evaporation of the dioxan, the residue is distilled. The main fraction, having a boiling point of 110° C/0.05 mm, contains 46 g of 3-aza-1-(1-cyclohexenyl)-spiro[5,5]undecane, which corresponds to a yield of 95 %.

EXAMPLE 6

60 g of 2-(1-cyclohexenyl)-3,3-pentamethylene-glutaric acid dinitrile are intensely shaken for 12 hours at 190° C and a hydrogen pressure of 260 bars in a V4A autoclave in the presence of 3 g of a catalyst containing 45 % of cobalt and 55 % of SiO$_2$. The reaction mixture contains 49 g of 3-aza-1-(1-cyclohexenyl)-spiro[5,5]undecane, which corresponds to a yield of 85 %.

What is claimed is:

1. 1,5-diamino-2-(1-cyclohexenyl)-3,3-pentamethylenepentane of the formula

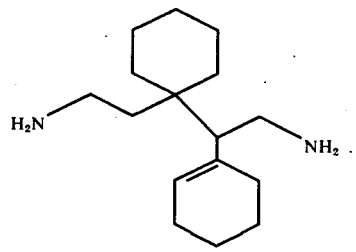

2. A process for the preparation of the diamine 1,5-diamino-2-(1-cyclohexenyl)-3,3-pentamethylene-pentane of the formula

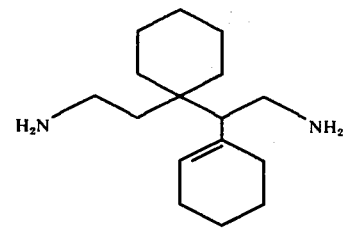

which process comprises dimerizing cyclohexylidene-acetonitrile in the liquid phase in the presence of a basic catalyst at a temperature of from about 0° to about 200° C. to form the dinitrile 2-(1-cyclohexenyl)-3,3-pentamethylene-glutaric acid dinitrile of the formula

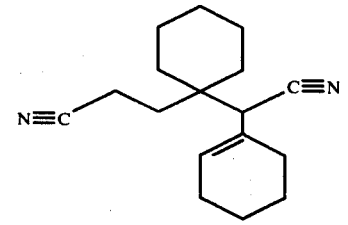

hydrogenating said dinitrile in the presence of a hydrogenation catalyst at a temperature of from about 90° to about 150° C. to form said diamine, and isolating said diamine from the reaction mixture.

3. A process according to claim 2 wherein said diamine is prepared in a solvent mixture of dioxane and liquid ammonia.

4. A process according to claim 2 wherein said basic catalyst is an alcoholate, an amide or a hydride of an alkali metal or of an alkaline earth metal.

5. A process according to claim 2 wherein said basic catalyst is used in an amount of from about 0.1 to about 10 mol percent based on said cyclohexylidene-acetonitrile.

6. A process according to claim 2 wherein said hydrogenation catalyst contains platinum, rhodium, ruthenium, palladium, nickel or cobalt.

7. A process according to claim 2 wherein said hydrogenation catalyst is used in an amount of from about 0.1 to about 20 grams per mol of said dinitrile.

8. A process according to claim 2 wherein said dinitrile is hydrogenated at a pressure of from about 50 to about 500 bars.

9. A process according to claim 2 wherein said dinitrile is hydrogenated in methanol, ethanol, hexane, acetic acid, tetrahydrofuran, acetic acid ethyl ester, dioxane, liquid ammonia or mixtures thereof as solvent.

* * * * *